United States Patent [19]

Ike et al.

[11] Patent Number: 5,703,150

[45] Date of Patent: Dec. 30, 1997

[54] PHOSPHONITE OR PHOSPHONATE COMPOUNDS AND USE THEREOF

[75] Inventors: Tetsuji Ike; Takeshi Inoue, both of Fukuoka; Yoshihiro Ozaki, Osaka, all of Japan

[73] Assignee: Yoshitomi Pharmaceutical Industries, Ltd., Osaka, Japan

[21] Appl. No.: 579,256

[22] Filed: Dec. 27, 1995

[30] Foreign Application Priority Data

Dec. 28, 1994 [JP] Japan ..................... 6-328039

[51] Int. Cl.⁶ ................. C08J 3/00; C07F 9/02
[52] U.S. Cl. ............... 524/125; 252/400.23; 524/125; 524/126; 524/128; 558/156; 558/162
[58] Field of Search .................. 524/125, 126, 524/128; 252/400.23; 558/156, 162

[56] References Cited

U.S. PATENT DOCUMENTS

| | | | |
|---|---|---|---|
| 3,825,629 | 7/1974 | Hofer et al. | 260/932 |
| 3,928,510 | 12/1975 | Hofer et al. | 260/962 |
| 3,954,847 | 5/1976 | Hofer et al. | 260/502.4 P |
| 3,962,175 | 6/1976 | Hofer et al. | 260/45.7 P |
| 4,075,163 | 2/1978 | Hofer et al. | 260/45.7 P |
| 4,115,639 | 9/1978 | Brown et al. | 526/130 |
| 4,261,880 | 4/1981 | Fujii et al. | 260/45.8 |
| 4,952,649 | 8/1990 | Kioka et al. | 526/125 |
| 5,109,043 | 4/1992 | Böhshar et al. | 524/126 |
| 5,300,257 | 4/1994 | Akashi et al. | 252/400.24 |
| 5,342,869 | 8/1994 | Stoll et al. | 524/125 |

FOREIGN PATENT DOCUMENTS

| | | |
|---|---|---|
| 1 372 528 | 10/1974 | United Kingdom. |
| 2 215 727 | 9/1989 | United Kingdom. |
| 2 227 490 | 8/1990 | United Kingdom. |
| 2 276 387 | 9/1994 | United Kingdom. |

OTHER PUBLICATIONS

Kaminsky et al., Journal of Polymer Science: Polymer Chemistry Edition, vol. 23, pp. 2151–2164 (1985).

*Primary Examiner*—Sharon Gibson
*Assistant Examiner*—Deanna Baxam
*Attorney, Agent, or Firm*—Wenderoth, Lind & Ponack

[57] ABSTRACT

Phosphonite and phosphonate compounds

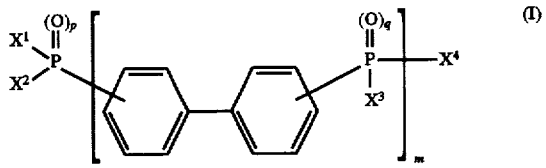

wherein $X^1$, $X^2$, $X^3$ and $X^4$ are each independently a group of the formula

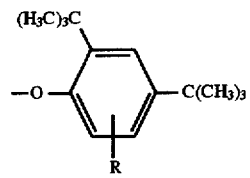

wherein R is a hydrogen atom or a methyl group, p is 0 or 1, q is independently 0 or 1 with regard to each repeat unit, and m is an integer of 2 to 10, a stabilizer for organic materials comprising said compound and a stabilized organic material comprising said compound. The compound of the present invention is less volatile at high temperatures. The use of the compound of the present invention as a stabilizer for organic materials affords an extremely useful organic material which is superior in heat stability and free of degradation caused by oxidation. The compound of the present invention has excellent compatibility with the above-mentioned organic materials and hardly migrate from the organic materials. Thus, the compound of the present invention can reside in the organic material for a prolonged period of time, which in turn stabilizes the organic materials in a sustained manner.

3 Claims, No Drawings

PHOSPHONITE OR PHOSPHONATE COMPOUNDS AND USE THEREOF

FIELD OF THE INVENTION

The present invention relates to novel phosphinite and phosphonate compounds useful as a stabilizer for organic materials, and use thereof.

BACKGROUND OF THE INVENTION

Organic materials such as natural polymer, synthetic polymer, fats and oils, lubricant oil and working oil are subject to oxidation which reduces utility thereof. Therefore, various antioxidants are devised and added to such organic materials. For example, it is known that addition of hindered phenol compounds, thioalkane ester compounds, organic phosphorus compounds and aromatic amines alone or in combination provides a stabilizing effect. In particular, synthetic resins such as polyethylene, polypropylene, acrylonitrile-butadiene-styrene resin and polyvinyl chloride resin are degraded by the action of heat, oxygen and light, and show color change and decreased mechanical strength to result in extremely shorter service life. For the prevention of the degradation, various kinds of antioxidants have been developed, of which phosphorus antioxidants have been widely used since they prevent color change of resins and increase heat resistance and weatherability thereof. There has been an increasing demand for an antioxidant which is superior in stability during processing and has a heat resistance capable of inhibiting volatilization thereof at high temperatures, since high temperature is used for high speed forming and for forming an alloy with engineering plastic and the like. To fulfill such needs, phosphites and phosphonite compounds have been developed and put on the market as phosphorus antioxidants. For example, UK patent No. 1372528 discloses 4,4'-biphenylenediphosphonite compounds represented by tetrakis(2,4-di-tert-butylphenyl)-4,4'-biphenylenediphosphonite; GB-A-2215727 discloses a composition containing tetrakis(2,4-di-tert-butylphenyl)-4,4'-biphenylenediphosphonite and a monophosphonite corresponding thereto;. GB-A-2227490 discloses a composition containing tetrakis(2,4-di-tert-butyl-6-methylphenyl)-4,4,'-biphenylenediphosphonite; U.S. Pat. No. 5342869 discloses a composition containing tetrakis(2,4-di-tert-butylphenyl)-4,4'-biphenylene-diphosphonate; and U.S. Pat. No. 5300257 discloses tetrakis(2,4-di-tert-butyl-5-methylphenyl)-4,4'-biphenylenediphosphonite.

None of these conventional phosphorus antioxidants is, however, necessarily satisfactory in terms of heat stability of the compound itself, and coloring-proof property and heat stability of the organic material composition containing such compound as an active ingredient. In addition, the stabilizing effect afforded by the above-mentioned compositions is not satisfactory.

Phosphorus antioxidants have been developed mainly for improving stabilization effect on organic materials, such as improved heat stability and weatherability to prevent coloring of the organic material. However, they suffer from the defect that the phosphorus antioxidants migrate out from the organic materials so that the effects of the antioxidants disappear at an early stage.

It is therefore an object of the present invention to provide novel phosphonite and phosphonate compounds which are superior in heat stability of themselves, which can provide organic materials with superior stabilizing effect and which are capable of maintaining antioxidant effect with controlled migration thereof from the organic materials, and use thereof.

According to the present invention, there are now provided phosphonite and phosphonate compounds having particularly superior heat stability, which greatly improve heat stability of organic materials when added thereto, and which are capable of maintaining antioxidant effect with controlled migration thereof from organic materials when added thereto.

The present invention provides the following.

(1) Phosphonite and phosphonate compounds of the formula (I)

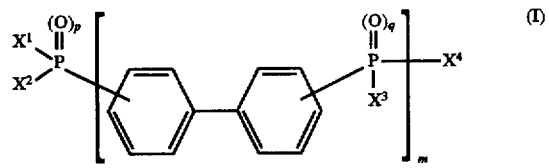

wherein $X^1$, $X^2$ and $X^4$ are each independently a group of the formula

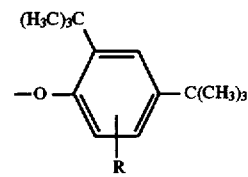

wherein R is a hydrogen atom or a methyl group, $X^3$ is independently, with regard to each repeat unit, a group of the formula

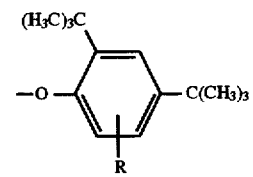

wherein R is a hydrogen atom or a methyl group, p is 0 or 1, q is independently 0 or 1 with regard to each repeat unit, and m is an integer of 2–10 [hereinafter also referred to as compound (I)].

(2) Phosphonite and phosphonate compounds of the formula (II)

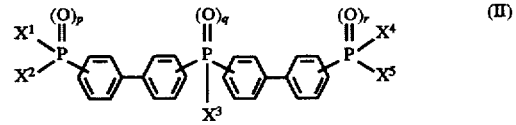

wherein $X^1$, $X^2$, $X^3$, $X^4$ and $X^5$ are each independently a group of the formula

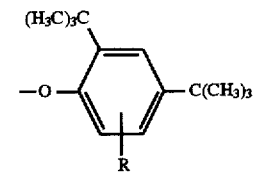

wherein R is a hydrogen atom or a methyl group, and p, q and r are each independently 0 or 1 (hereinafter also referred to as compound (II)).

(3) Phosphonite and phosphonate compounds of the formula (III)

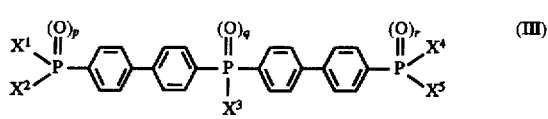 (III)

wherein $X^1$, $X^2$, $X^3$, $X^4$ and $X^5$ are each independently a group of the formula

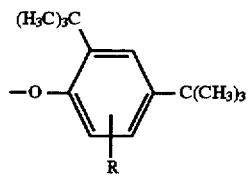

wherein R is a hydrogen atom or a methyl group, and p, q and r are each independently 0 or 1 [hereinafter also referred to as compound (III)].

(4) Stabilizers for organic materials, comprising a phosphonite or a phosphonate compound represented by compound (I), compound (II) or compound (III).

(5) Stabilized organic materials comprising a phosphonite or a phosphonate compound represented by compound (I), compound (II) or compound (III).

(6) Stabilizers for organic materials, comprising a phosphonite or a phosphonate compound represented by compound (I), compound (II) or compound (III), and at least one member selected from phenolic antioxidants, sulfuric antioxidants, ultraviolet absorbers, light stabilizers and phosphoric antioxidants.

(7) Stabilized organic materials comprising a phosphinite or a phosphonate compound represented by compound (I), compound (II) or compound (III), and at least one member selected from phenolic antioxidants, sulfuric antioxidants, ultraviolet absorbers, light stabilizers and phosphoric antioxidants.

In the compounds represented by compound (I), compound (II) or compound (III), the atomic value of respective phosphorus atoms is independently trivalent of pentavalent, namely,

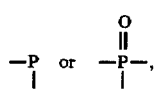

and R of a compound of the formula:

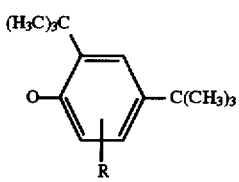

which is bonded to each phosphorus atom, is independently a hydrogen atom or a methyl group, and m is preferably 2–5, more preferably 2 or 3.

The compounds represented by compound (I), compound (II) or compound (III) are produced, for example, by the following method.

Biphenyl and halogenated phosphorus (e.g. phosphorus trichloride, phosphorus tribromide and phosphorus triiodide) are reacted in a gaseous phase at a high temperature or in the presence of a catalyst such as Lewis acid (e.g. aluminum chloride, aluminum bromide, aluminum iodide, gallium chloride, gallium bromide, indium chloride, indium bromide, tin chloride, titanium chloride, zirconium chloride, rhodium chloride, antimony fluoride, antimony chloride, tungsten chloride, iron chloride, zinc chloride, boron fluoride, boron chloride and niobium chloride), in a solvent (e.g. benzene, toluene, hexane, heptane, diethyl ether, tetrahydrofuran, chloroform, carbon tetrachloride, dichloroethane and chlorobenzene), preferably using the above-exemplified halogenated phosphorus as a solvent, under cooling or at a temperature in the range of from room temperature to the boiling point of the solvent used, preferably under reflux with heating, and a biphenylhalophosphine obtained and a stoichiometrical amount or more of a compound of the formula

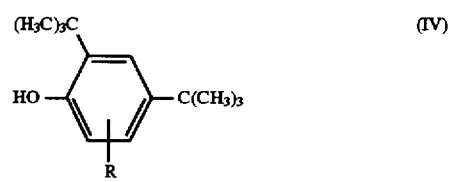 (IV)

wherein R is a hydrogen or a methyl group (hereinafter also referred to as compound (IV)) are reacted in the presence of an amine such as dimethylformamide, triethylamine, tributylamine, morpholine, dimethylaniline, pyridine, quinoline, collidine, aminopyridine, 1,8-bis(dimethylamino) naphthalene and 1,8-diazabicyclo [5.4.0]undec-7-en in a solvent such as benzene, toluene, hexane, heptane, diethyl ether, tetrahydrofuran, chloroform, carbon tetrachloride, dichloroethane, chlorotoluene and chlorobenzene under cooling or at a temperature in the range of from room temperature to the boiling point of the solvent used, for 30 minutes to 24 hours to give the compound of the present invention. Examples of the compound (IV) include 2,4-di-tert-butylphenol, 2,4-di-tert-butyl-5-methylphenol and 2,4-di-tert-butyl-6-methylphenol.

The obtained object compound can be purified by a conventional method such as recrystallization and chromatography.

The compounds represented by compound (I), compound (II) or compound (III) include, for example, the following compounds a to r, with preference given to compounds a to c.

In these compounds, respective phosphorus atoms may be

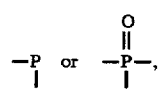

and R of a compound of the formula:

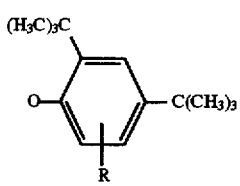

which is bonded to each phosphorus atom, may be a hydrogen atom, a methyl group at the 5 position or a methyl group at the 6 position.

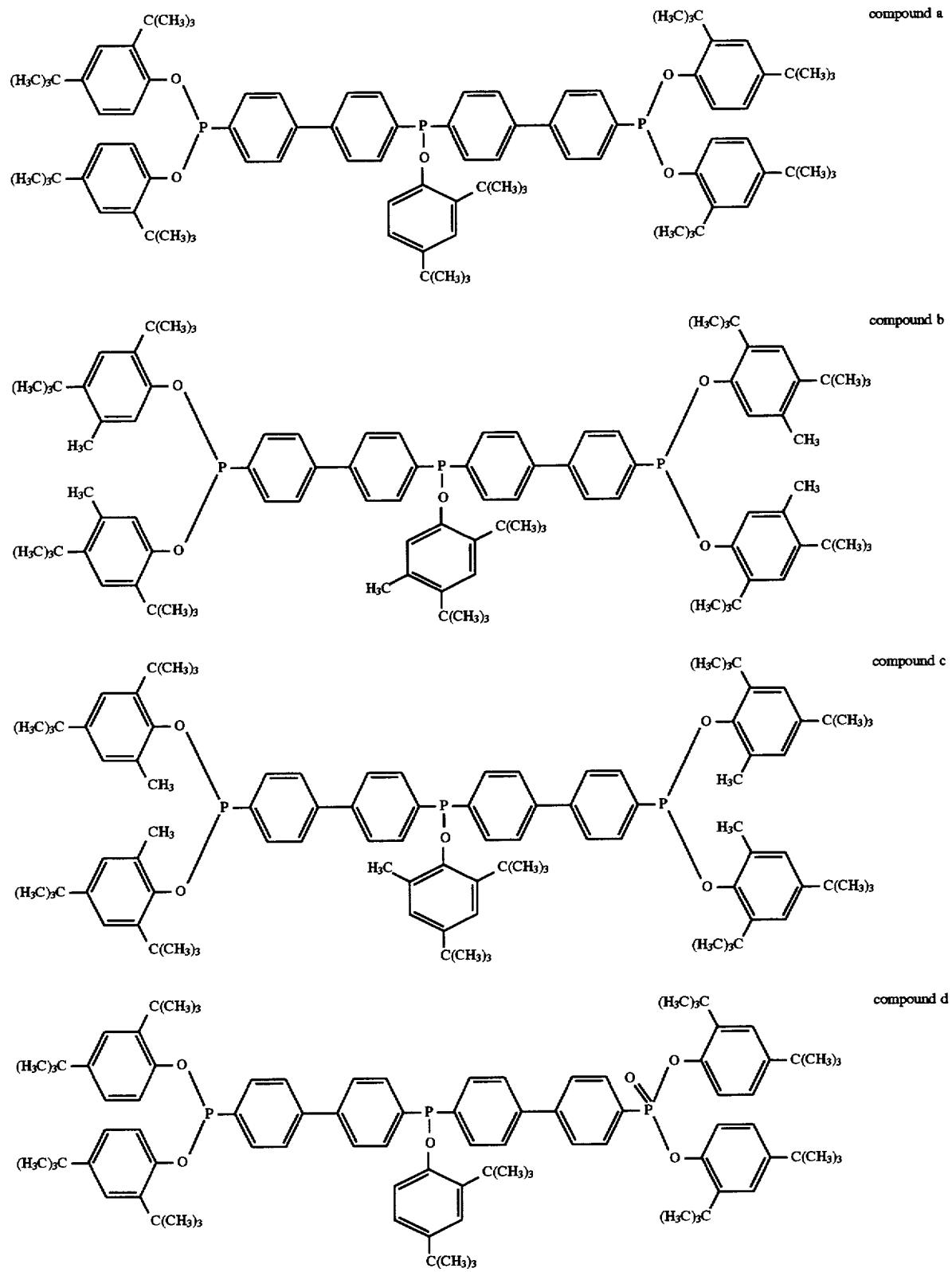

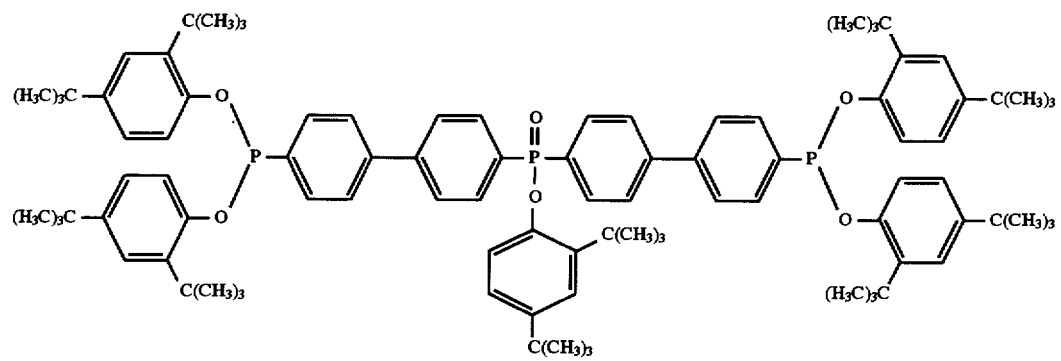
compound e
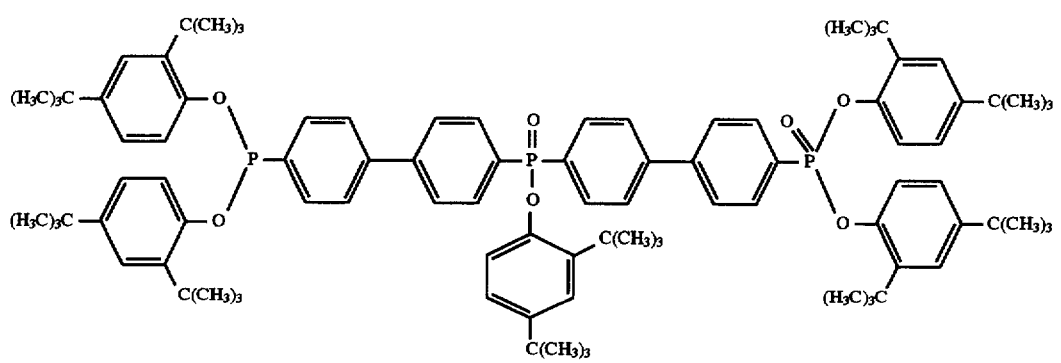
compound f
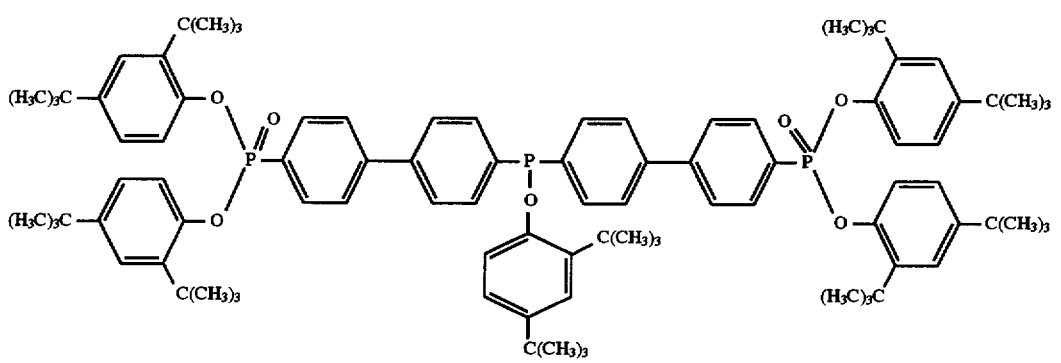
compound g
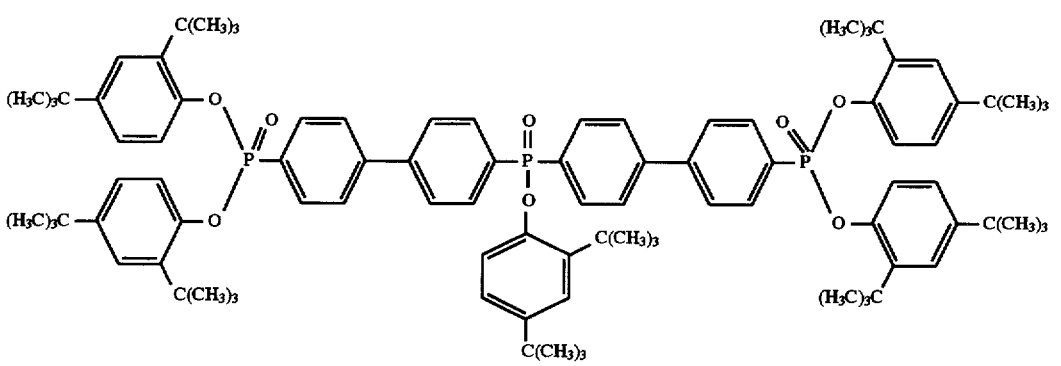
compound h

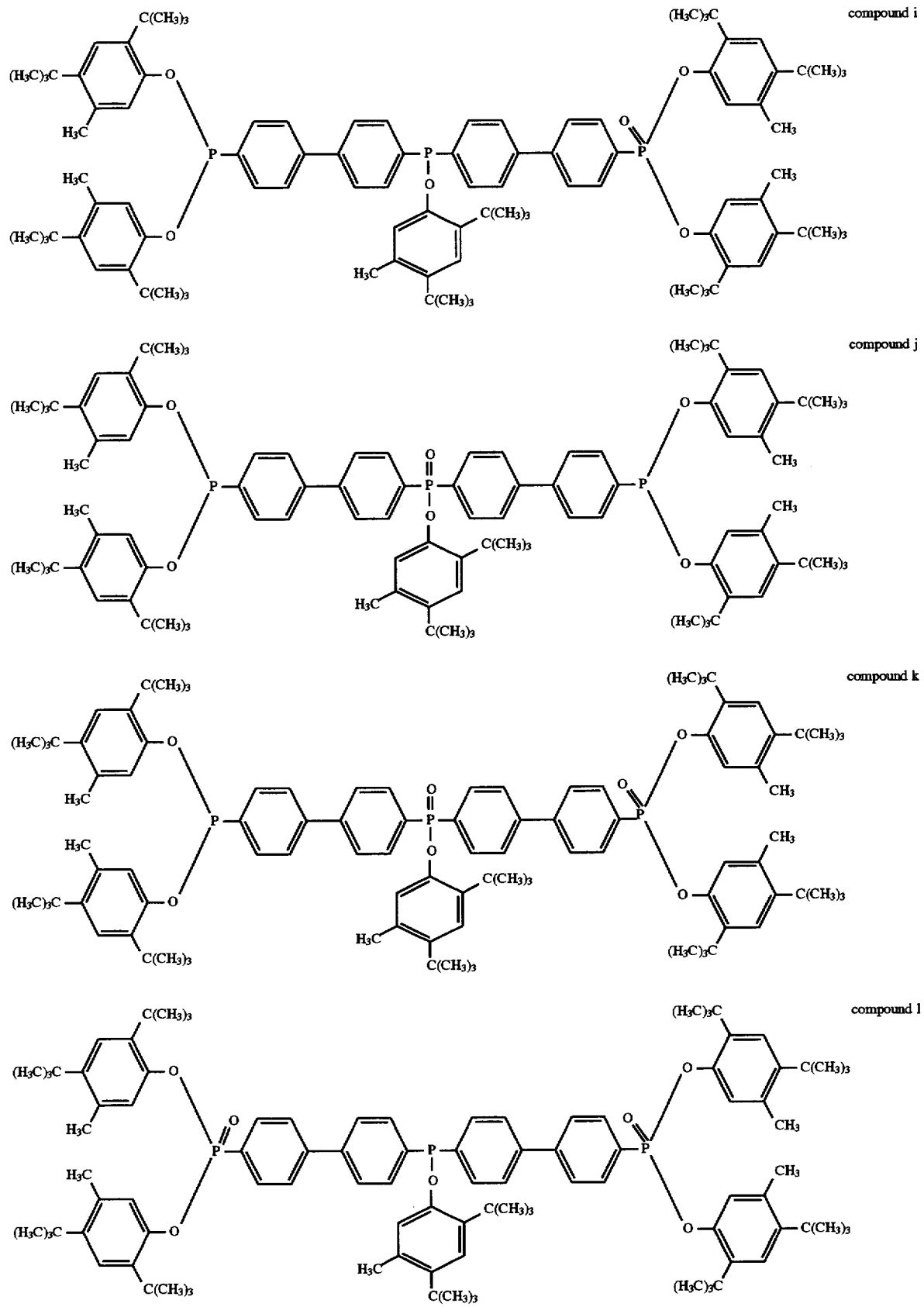

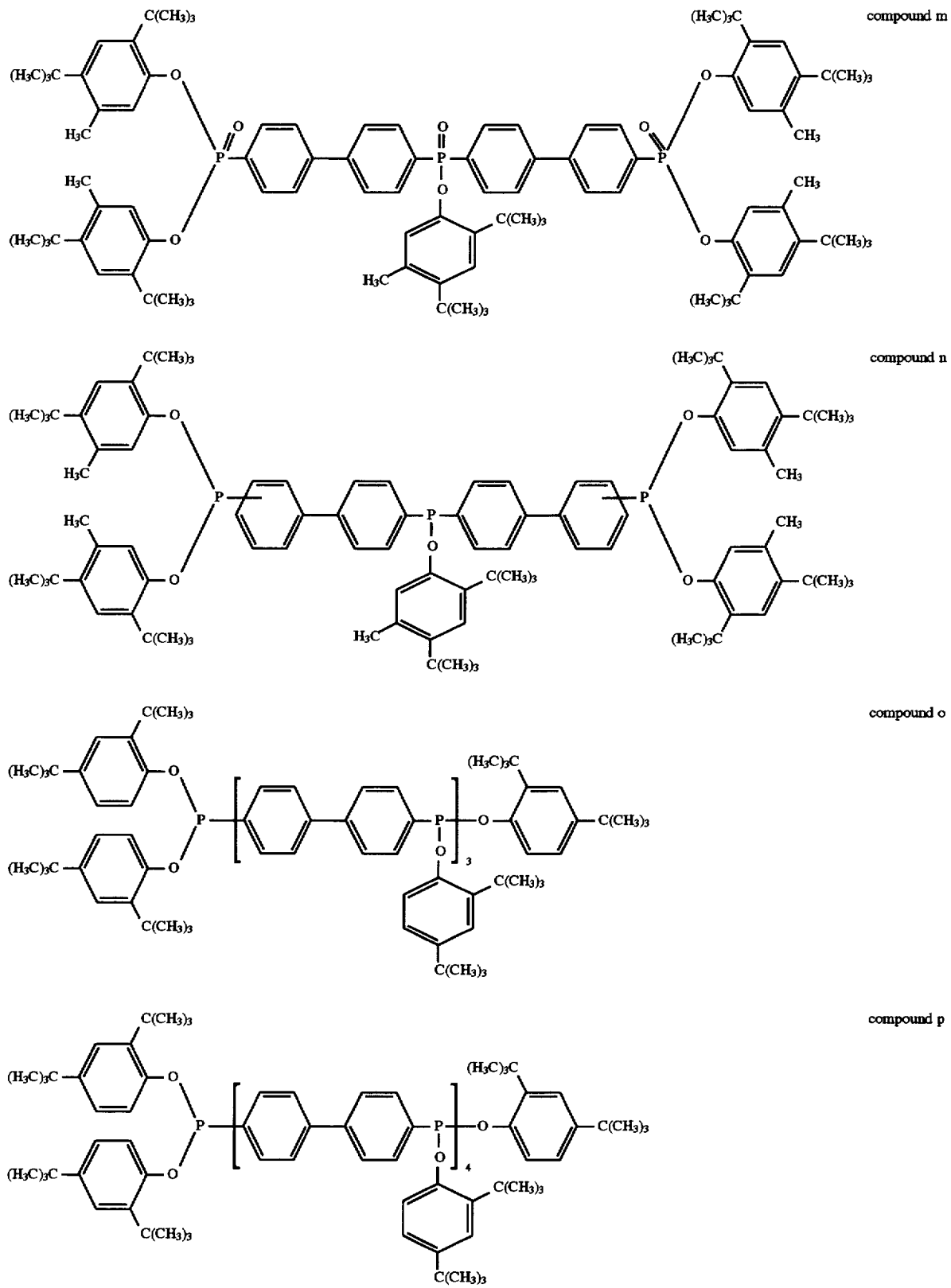

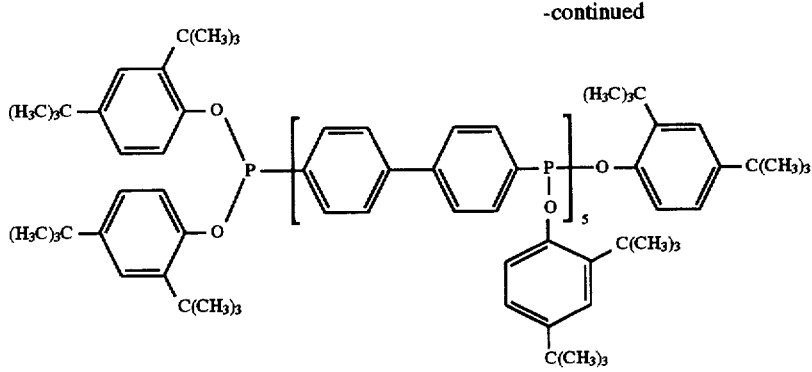

compound q

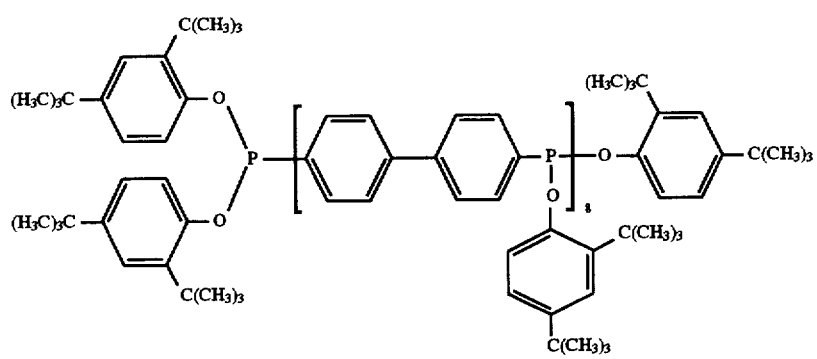

compound r

The compound (I), compound (II) and compound (III) of the present invention have particularly superior heat stability and show less volatilization at high temperatures. They are useful as stabilizers to prevent degradation of organic materials caused by oxidation and compounds a to c are notably useful. The compound (I), compound (II) and compound (III) of the present invention may be used alone or in combination with or by mixing with, for example, one or more members selected from compounds d, e, f, g and h in the case of compound a; and one or more members selected from compounds i, j, k, l and m in the case of compound b. In addition, compounds n to r may be used in combination with or upon mixing with the compound a or b.

The organic materials to be stabilized by the compound of the present invention are exemplified by macromolecular polymers, fats and oils, mineral oils themselves and those comprising them, and examples of the macromolecular polymer include polyolefines, halogen-containing synthetic resins, petroleum resins, coumarone resins, polystyrene, styrene copolymers, styrene resins, vinyl polyacetate, polyvinyl alcohol, polyvinyl formal, polyvinyl butyrate, acrylic resins, methacrylic resins, polyacrylonitrile resins, straight-chain polyesters, polyphenylene oxide, polyamide, polycarbonate, modified polyphenylene oxide, polyacetal, polyurethane, cellulose resins, unsaturated polyester resins, phenol resins, urea resins, melamine resins, epoxy resins, silicon resins, polyethylene terephthalate, reinforced polyethylene terephthalate, polybutyrene terephthalate, polysulfone resins, polyether sulfone, polyphenylene sulfide, polyether ketone, polyetherimide, polyoxybenzoyl, polyimide, polymaleimide, polyamideimide, natural rubber, synthetic rubber and a blend of these.

Examples of polyolefine include polyethylene (e.g. high density polyethylene, low density polyethylene, linear low density polyethylene and linear medium density polyethylene), α-olefine polymers such as polypropylene, polybutene, polypentene and poly-3-methylbutylene, mixtures of polystyrene with polyethylene, polypropylene and/ or other compatible polymers, and ethylene-vinyl acetate copolymers and ethylene-propylene copolymers. The aforementioned polyolefines may be those purified, after polymerization, to a small degree by removing residual catalyst, or those relatively highly purified, or polyolefines containing residual catalyst, which have undergone no removal process or only a simplified removal process for a highly active catalyst only to used. In particular, there can be used crystalline polyolefines obtained by using Ziegler type catalyst or chromium type catalyst where a halogen-containing magnesium compound is used as a catalyst carrier, and from which residual catalyst has not been removed yet (see U.S. Pat. Nos. 4,261,880, 4,952,649 and 4,115,639). In addition, they may be a polyolefine having a very narrow molecular weight distribution which is obtained using a metallocene single site catalyst (Journal of Polymer Science Polymer Chemistry Edition, vol. 23, 2151 (1985)).

Examples of halogen-containing resin include poly(vinyl chloride), poly(vinyl bromide), poly(vinyl fluoride), poly (vinylidene chloride), poly(vinylidene fluoride), chlorinated polyethylene, chlorinated polypropylene, brominated polyethylene, chlorinated rubber, vinyl chloride-vinyl acetate copolymers, vinyl chloride-ethylene copolymers, vinyl chloride-propylene copolymers, vinyl chloride-styrene copolymers, vinyl chloride-isobutylene copolymers, vinyl chloride-vinylidene chloride copolymers, vinyl chloride-styrene-maleic anhydride terpolymers, vinyl chloride-styrene-acrylonitrile terpolymers, vinyl chloride-butadiene copolymers, vinyl chloride-isobutylene copolymers, vinyl chloride-chlorinated propylene copolymers, vinyl chloride-vinylidene chloride-vinyl acetate terpolymers, vinyl chloride-acrylate copolymers, vinyl chloride-maleate copolymers, vinyl chloride-methacrylate copolymers, vinyl chloride-acrylonitrile copolymers and internally plasticized poly(vinyl chloride).

Examples of styrene copolymer include copolymers of styrene and other monomer (e.g. maleic anhydride, butadiene and acrylonitrile).

Examples of styrene resin include acrylonitrile-butadiene-styrene resin, acrylate-butadiene-styrene resin and methacrylate-butadiene-styrene resin.

Synthetic rubber include, for example, isoprene rubber, butadiene rubber and acrylonitrile-butadiene copolymer rubber.

Of the organic materials to be stabilized by the compound of the present invention, preferred are the above-mentioned macromolecular polymers, with preference given to polyolefines such as polyethylenes (e.g. high density polyethylene, low density polyethylene, linear low density polyethylene and linear medium density polyethylene) and polypropylene, poly(vinyl chloride), acrylonitrile-butadiene-styrene resin, polycarbonate and modified polyphenylene oxide.

The compound of the present invention has excellent compatibility with the above-mentioned organic materials and hardly migrate from the organic materials. Thus, the compound of the present invention can reside in the organic material for a prolonged period of time, which in turn stabilizes the organic materials in a sustained manner.

When the compound of the present invention is used as a stabilizer for organic materials, it is preferably added in a proportion of 0.01–10% by weight relative to the organic materials, more preferably in a proportion of 0.01–5% by weight relative to the organic materials.

The stabilizer compound of the present invention in combination with phenolic antioxidants and/or sulfuric antioxidants gives superior heat stability to organic materials. When the compound of the present invention is combined with one or more of the phenolic antioxidants and/or sulfuric antioxidants and used as a stabilizer for organic materials, said antioxidants are preferably added respectively in a proportion of 0.01–10% by weight relative to the organic materials, more preferably in a proportion of 0.01–5% by weight relative to the organic materials. When the combined use is employed, these components can be added separately or may be added to a mixture of the compound of the present invention and antioxidants other than those mentioned above. In so doing, the other antioxidants are added in a 0.1 to 10-fold amount relative to the compound of the present invention.

The phenolic antioxidants include, but not limited to, 2,6-di-tert-butyl-4-methylphenol, 4-hydroxymethyl-2,6-di-tert-butylphenol, 2,6-di-tert-butyl-4-ethylphenol, butylated hydroxyanisole, n-octadecyl 3-(4-hydroxy-3,5-di-tert-butylphenyl)propionate, distearyl (4-hydroxy-3-methyl-5-tert-butyl)benzylmalonate, propyl gallate, octyl gallate, dodecyl gallate, tocopherol, 2-2'-methylenebis(4-methyl-6-tert-butyl-phenol), 2,2'-methylenebis(4-ethyl-6-tert-butylphenol), 4,4'-methylenebis(2,6-di-tert-butylphenol)4, 4'-butylidenebis(6-tert-butyl-m-cresol), 4,4'-thiobis(6-tert-butyl-m-cresol), styrinated phenol, N,N'-hexamethylenebis (3,5-di-tert-butyl-4-hydroxyhydrocinnamide), calcium bis (3,5-di-tert-butyl-4-hydroxybenzylphosphonic acid ethyl ester), 1,1,3-tris(2-methyl-4-hydroxy-5-tert-butylphenyl) butane, 1,3,5-trimethyl-2,4,6-tris(3,5-di-tert-butyl-4-hydroxybenzyl)benzene, tetrakis[3-(3,5-di-tert-butyl-4-hydroxyphenyl)propionyloxymethyl]-methane, 1,6-hexanediolbis[3-(3,5-di-tert-butyl-4-hydroxyphenyl)-propionate], 2,2'-methylenebis(4-methyl-6-cyclohexylphenol), 2,2'-methylenebis[6-(1-methylcyclohexyl)-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)isocyanuric acid, triethylene glycol-bis|3-(3-tert-butyl-4-hydroxy-5-methylphenyl)propionate], 2,2'-oxamide-bis[ethyl 3-(3,5-di-tert-butyl-4-hydroxyphenyl)propionate], 6-(4-hydroxy-3,5-di-tert-butylanilino)-2,4-dioctylthio-1,3,5-triazine, bis[2-tert-butyl-4-methyl-6-(2-hydroxy-3-tert-butyl-5-methylbenzyl)phenyl]terephthalate, 3,9-bis[2-[3-(3-tert-butyl-4-hydroxy-5-methylphenyl) propionyloxy]-1,1-dimethylethyl]-2,4,8,10-tetraoxaspiro[5.5]undecane or 3,9-bis[2-[3-(3,5-di-tert-butyl-4-hydroxyphenyl)propionyloxy]-1,1-dimethylethyl]2,4,8,10-tetraoxaspiro[5,5]undecane.

The preferable phenolic antioxidants include 2,6-di-tert-butyl-4-methylphenol, n-octadecyl 3-(4-hydroxy-3,5-di-tert-butylphenyl)-propionate, tetrakis[3-(3,5-di-tert-butyl-4-hydroxyphenyl)propionyloxy-methyl]methane, triethylene glycol-bis [3-(3-tert-butyl-4-hydroxy-5-methylphenyl) propionate, 4,4'-butylidenebis (6-tert-butyl-m-cresol), 4,4'-thiobis(6-tert-butyl-m-cresol), 1,3,5-tris(3,5-di-tert-butyl-4-hydroxybenzyl) isocyanuric acid, 1,1,3-tris (2-methyl-4-hydroxy-5-tert-butyl-phenyl) butane or 3,9-bis[2-[3-(3-tert-butyl-4-hydroxy-5-methylphenyl) -propionyloxy]-2,4,8,10-tetraoxaspiro[5.5]undecane.

The sulfuric antioxidant is an ester of thioalkanoic acid, such as dilauryl ester, dimyristyl ester, distearyl ester and didocosyl ester, and an ester with polyhydric alcohol such as glycerol, trimethylolethane, trimethylolpropane, pentaerythritol and trishydroxyethylisocyanurate.

Preferable sulfuric antioxidants are dilauryl thiodipropionate, dimyristyl thiodipropionate, distearyl thiodipropionate and pentaerythritol-tetrakis(β-lauryl thiopropionate).

Also, ultraviolet absorbers and light stabilizers can be used in combination with the stabilizer compound of the present invention for improving weather resistance of the organic materials.

Examples of such ultraviolet absorber and light stabilizer include salicylic acid compounds, benzophenone compounds, benzotriazole compounds, cyanoacrylate compounds, nickel compounds and 2,2,6,6-tetramethylpiperidine compounds such as phenyl salicylate, p-tert-butylphenyl salicylate, p-octylphenyl salicylate, 2,4-dihydroxybenzophenone, 2-hydroxy-4-acetoxyethoxybenzophenone, 2-hydroxy-4-methoxybenzophenone, 2,2'-dihydroxy-4,4'-dimethoxybenzophenone, 2-hydroxy-4-n-octyloxybenzophenone, 2-hydroxy-4-isooctyloxybenzophenone, 2-hydroxy-4-dodecyloxybenzophenone, 2-hydroxy-4-octadecyloxybenzophenone, disodium 2,2'-dihydroxy-4,4'-dimethoxy-5,5'-disulfobenzophenone, 2-hydroxy-4-(2-hydroxy-3-methacryloxy)propoxybenzophenone, 2-(2-hydroxy-5-methylphenyl)benzotriazole, 2- (2-hydroxy-3,5-di-tert-butylphenyl)benzotriazole, 2-(2-hydroxy-3-tert-butyl-5-methylphenyl)-5-chlorobenzotriazole, 2-(2-hydroxy-3,5-di-tert-butylphenyl)-5-chlorobenzotriazole, 2-[2-hydroxy-5-(1,1,3,3-tetramethylbutyl)phenyl] benzotriazole, n-hexadecyl 3,5-di-tert-butyl-4-hydroxybenzoate, 2,4-di-tert-butylphenyl 3,5-di-tert-butyl-4-hydroxybenzoate, ethyl 2-cyano-3,3-diphenylacrylate, nickel[2,2'-thiobis{4-(1,1,3,3-tetramethylbutyl)phenolate}]-n-butylamine, nickel [2,2'-thiobis{4-(1,1,3,3-tetramethylbutyl)phenolate}], nickel bis(3,5-di-tert-butyl-4-hydroxybenzylphosphonic acid ethyl ester), bis(2,2,6,6-tetramethyl-4-piperidyl) sebacate, bis(1,2,2,6,6-pentamethyl-4-piperidyl)-2-(3,5-di-tert-butyl-4-hydroxybenzyl)-2-n-butylmalonate, bis(1-acryloyl-2,2,6,6-tetramethyl-4-pyperidyl)bis-(3,5-di-tert-butyl-4-hydroxybenzyl)malonate, tetrakis(2,2,6,6-tetramethyl-4-piperidyl)-1,2,3,4-butanetetracarboxylate, poly{[6-(1,1,3,3-tetramethylbutyl) imino-s-triazine-2,4-diyl][(2,2,6,6-tetramethyl-4-piperidyl)imino]hexamethylene [(2,2,6,6- tetramethyl-4-piperidyl) imino]}, poly{(6-morpholino-s-triazine-2,4-diyl) [(2,2,6,6-tetramethyl-4-piperidyl)imino] hexamethylene [(2,2,6,6-tetramethyl-4-piperidyl) imino]}, condensate of 1-hydroxyethyl-2,2,6,6-tetramethyl-4-piperidinol and succinic acid, and condensate of cyanuric chloride, tertiary octylamine and 1,6-bis(2,2,6,6-tetramethyl-4-piperidylamino)hexane.

Preferred ultraviolet absorber and light stabilizer are, for example, 2-hydroxy-4-n-octyloxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-di-tert-butylphenyl)-5-chlorobenzotriazole, bis (2,2,6,6-tetramethyl-4-piperidyl)sebacate, poly-{[6-(1,1,3,3-tetramethylbutyl)imino-s-triazine-2,4-diyl][(2,2,6,6-tetramethyl-4-piperidyl)imino]hexamethylene [(2,2,6,6-tetramethyl-4-piperidyl)imino]}.

The compound of the present invention may be used in combination with other phosphorus antioxidants to prevent degradation by oxidation of organic materials, and such phosphorus antioxidants include, for example, tetrakis(2,4-di-tert-butylphenyl)-4,4'-biphenylenediphosphonite, tris(2,4-di-tert-butylphenyl)phosphite, bis(2,4-di-tert-butylphenyl)-4-biphenylphosphonite, tetrakis (2,4-di-tert-butyl-5-methylphenyl)-4,4'-biphenylenediphosphonite, tris (2,4-di-tert-butyl-5-methylphenyl)phosphite, bis (2,4-di-tert-butyl-5-methylphenyl)-4-biphenylphosphonite, tetrakis (2,4-di-tert-butyl-6-methylphenyl)-4,4'-biphenylenediphosphonite, tris(2,4-di-tert-butyl-6-methylphenyl)-phosphite, bis(2,4-di-tert-butyl-6-methylphenyl)-4-biphenylphosphonite, bis(2,4-di-tert-butylphenyl)pentaerythritoldiphosphite, 2,2'-methylenebis (4,6-di-tert-butylphenyl)-2-ethylhexylphosphite and mixtures thereof.

Preferable phosphoric antioxidants include, for example, tetrakis (2,4-di-tert-butylphenyl)-4,4'-biphenylenediphosphonite, tris(2,4-di-tert-butylphenyl) phosphite, bis(2,4-di-tert-butylphenyl)-4-biphenylphosphonite, tetrakis(2,4-di-tert-butyl-5-methylphenyl)-4,4-biphenylenediphosphonite, tris(2,4-di-tert-butyl-5-methylphenyl)phosphite, bis(2,4-di-tert-butyl-5-methylphenyl) -4-biphenylphosphonite, tetrakis(2,4-di-tert-butyl-6-methylphenyl)-4,4'-biphenylenediphosphonite, tris(2,4-di-tert-butyl-6-methylphenyl)-phosphite, bis (2,4-di-tert-butyl-6-methylphenyl)-4-biphenylphosphonite and mixtures thereof.

When compound a is used as a stabilizer for organic materials, one or more members selected from 2,4-di-tert-butylphenol, bis(2,4-di-tert-butylphenyl)-4-biphenylphosphonite, tris(2,4-di-tert-butylphenyl) phosphite, tetrakis(2,4-di-tert-butylphenyl)-4,4'-biphenylenediphosphonite,tetrakis(2,4-di-tert-butylphenyl)-4,4'-biphenylenediphosphonate and tetrakis(2,4-di-tert-butylphenyl)-4,4'-biphenylene-phosphonate-phosphonite may be used besides compound d, compound e, compound f, compound g and compound h. When compound b is used as a stabilizer for organic materials, one or more members selected from 2,4-di-tert-butyl-5-methylphenol, bis(2,4-di-tert5-methylphenyl)-4-biphenylphosphonite, tris(2,4-di-tert-butyl-5-methylphenyl)phosphite, tetrakis(2,4-di-tert-butyl-5-methylphenyl)-4,4'-biphenylenediphosphonite, tetrakis(2,4-di-tert-5-methylphenyl)-4,4'-biphenylenediphosphonate and tetrakis(2,4-di-tert-5-methylphenyl)-4,4'-biphenylenephosphonate-phosphonite may be used besides compound i, compound j, compound k, compound l and compound m. When compound c is used as a stabilizer for organic materials, one or more members selected from 2,4-di-tert-butyl-6-methylphenol, bis(2,4-di-tert-butyl-6-methylphenyl)-4-biphenylphosphonite, tris(2,4-di-tert-butyl-6-methylphenyl)phosphite, tetrakis(2,4-di-tert-butyl-6-methylphenyl)-4,4'-biphenylenediphosphonite, tetrakis(2,4-di-tert-butyl-6-methylphenyl)-4,4'-biphenylenediphosphonate and tetrakis(2,4-di-tert-butyl-6-methylphenyl)-4,4'-biphenylenephosphonate-phosphonite may be used besides compound c wherein phosphorus atom is respectively

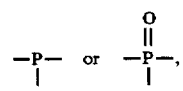

as in compound a and compound b.

In addition, phosphonite and phosphonate compounds having 4 or more phosphorus atoms such as compounds o–r can be used. Moreover, a compound other than 4,4'-biphenylenediphosphonite compound, such as 3,3'-biphenylenediphosphonite compound can be used as in the case of compound n.

When the compound of the present invention is used in combination with one or more ultraviolet absorbers, light stabilizers and phosphoric antioxidants, as a stabilizer for organic materials, said stabilizers are each preferably added respectively in a proportion of 0.01–10% by weight relative to the organic materials, more preferably in a proportion of 0.01–5% by weight relative to the organic materials.

As described, the present invention provides a stabilizer for organic materials, comprising one or more compounds of the present invention and at least one member selected from phenolic antioxidants, sulfuric antioxidants, ultraviolet absorbers, light stabilizers and phosphoric antioxidants. The present invention also provides organic materials comprising such stabilizers.

The method for adding one or more compounds of the present invention or a mixture of the compound of the present invention and one or more other stabilizers such as antioxidants, ultraviolet absorbers and light absorbers includes, for example, mixing, kneading and extrusion.

The compound of the present invention can be used in combination with, for example, metal soaps such as calcium stearate, heavy metal inactivators such as hydrazo compound, nucleators such as aluminumhydroxy-di-p-tert-butylbenzoate, organic tin stabilizers such as monobutyltinoxide and dibutyltinoxide, plasticizers such as di-2-ethylhexyl phthalate and di-2-ethylhexyl adipate, epoxy compounds such as epoxysoybean oil and epoxyoctyl stearate, various organic pigments, fillers such as aluminum oxide, foaming agents such as sodium bicarbonate and azodicarbonamide, antistatic agents such as anionic/cationic surfactant, flame retarders such as phosphoric ester, lubricants such as aliphatic amide and fatty acid lower alcohol ester and acrylic polymer processing aids.

The present invention is described in detail in the following by illustrative Examples and Experimental Examples, to which the present invention is not limited.

EXAMPLE 1
Production of (compound a) of the formula:

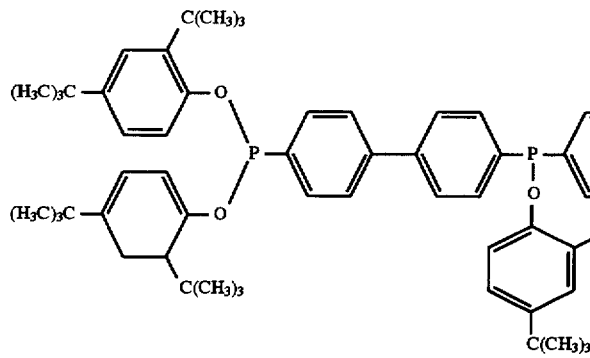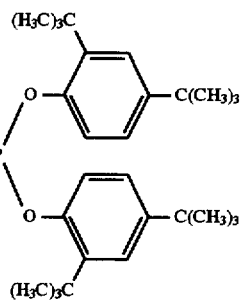

(1) Aluminum chloride (38.5 g) was added to biphenyl (16.9 g) and phosphorus trichloride (58 g) and the mixture was refluxed under heating for 8 hours. After cooling, excess phosphorus trichloride was distilled away at 55°–90° C. under reduced pressure.

(2) A red mixture of biphenylchlorophosphine-aluminum chloride complex obtained in (1) was dropwise added to a solution of toluene (230 g), pyridine (69 g) and 2,4-di-tert-butylphenol (90.8 g) over one hour at 80° C., and allowed to reach for 5 hours at 80° C. Aluminum chloride-pyridine complex and pyridine hydrochloride were separated from the reaction product and treated with an adsorbent. The solvent was concentrated under reduced pressure and repeatedly purified from a mixed solvent of acetonitrile and toluene to give 4.6 g of a yellow powder. A portion thereof was purified by gel permeation chromatography to give a pale yellow powder having a melting point of 126°–139° C. The obtained compound was confirmed to be compound a by infrared absorption spectrum and nuclear magnetic resonance spectrum.

Liquid chromatography mass spectrum of this compound detected compound d, compound f and compound g besides compound a.

EXAMPLE 2
Production of (compound b) of the formula:

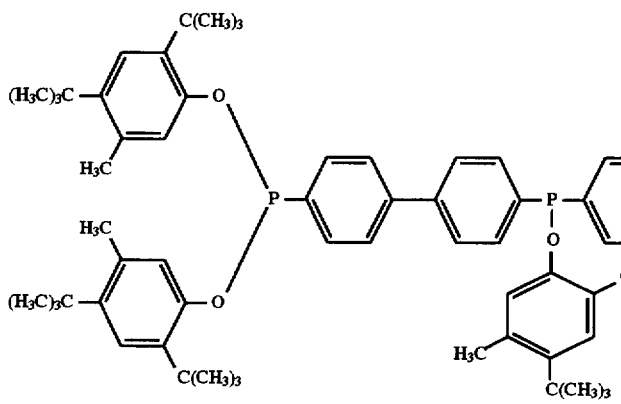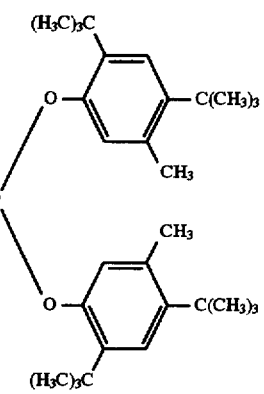

(1) Aluminum chloride (10.7 g) was added to biphenyl (4.6 g) and phosphorus trichloride (65.9 g) and the mixture was refluxed under heating for 10 hours. After cooling, the mixture was cooled to not more than 5° C. and phosphorus oxychloride (12.3 g) was dropwise added, which was followed by reaction for 0.5 hour. The aluminum chloride-phosphorus oxychloride complex was filtrated and thoroughly washed with chlorobenzene. The filtrate was concentrated under reduced pressure to give a red yellow viscous biphenylchlorophosphine mixture.

(2) 2,4-di-tert-Butyl-5-methylphenol (17.6 g) and triethylamine (8.1 g) were dissolved in toluene (80 g) and the mixture was cooled to not more than 5° C. A solution of biphenylchlorophosphine mixture (7.6 g) obtained in (1) in toluene (50 g) was dropwise added. The mixture was reacted at 40°–100° C. for 6 hours. After the reaction, the mixture was cooled and triethylamine hydrochloride was filtrated. The filtrate was concentrated under reduced pressure and repeatedly purified from a mixed solvent of acetonitrile and toluene to give 5.5 g of a yellow powder. A portion thereof was purified by gel permeation chromatography to give a pale yellow powder having a melting point of 134°–148° C. The obtained compound was confirmed to be compound b by infrared absorption spectrum and nuclear magnetic resonance spectrum.

Liquid Chromatography mass spectrum of this compound detected compound i, compound k and compound l besides compound b.

The effect of the present invention is explained by the following Experimental Examples.

Experimental Example 1: Heat volatility

The temperature (° C.) at which the weight decrease began and the temperature (° C.) at which the weight reduced to 50% were determined by thermogravimetric analysis in a nitrogen atmosphere at a temperature elevating speed of 10° C./min. In Table 1, Comparative Examples 1 to 3 are the following compounds (the same in the following Experimental Examples 2 and 3).

21

Comparative Example 1: tetrakis(2,4-di-tert-butylphenyl)-4,4'-biphenylenediphosphonite Comparative Example 2: tetrakis(2,4-di-tert-butyl-5-methylphenyl)-4,4'-biphenylenediphosphonite Comparative Example 3: tris(2,4-di-tert-butylphenyl) phosphite The results are shown in Table 1.

TABLE 1

| | Temperature at initiation of weight reduction (°C.) | Temperature at 50% reduction (°C.) |
|---|---|---|
| Compound of Ex. 2 | 330 | 430 |
| Comparative Ex. 1 | 218 | 392 |
| Comparative Ex. 2 | 293 | 412 |
| Comparative Ex. 3 | 184 | 308 |

As shown in Table 1, the compound of the present invention was superior in high temperature volatility as compared with the compounds of Comparative Examples, and retained heat stability.

EXPERIMENTAL EXAMPLE 2

A composition having the formulation of the following Formulation Example was added to a polypropylene (homopolymer) resin without additives, and the mixture was mixed in a mixer for 5 minutes, after which pellets were extruded by an extruder (20 mmφ) at a die temperature of 280° C. Using these pellets, heat stability (determinations of oxygen absorption induction period at 190° C. by macromolecule degradation measurement apparatus) was determined.

Formulation Example:

| | |
|---|---|
| Polypropylene (homopolymer) resin | 99.7% by weight |
| Test Compound | 0.1% by weight |
| Tetrakis[3-(3,5-di-tert-butyl-4-hydroxyphenyl)propionyloxymethyl]methane | 0.1% by weight |
| Calcium stearate | 0.1% by weight |

The results are shown in Table 2.

TABLE 2

| | Oxygen absorption induction period (min) |
|---|---|
| Example 1 | 100 |
| Example 2 | 118 |
| Comparative Ex. 1 | 67 |
| Comparative Ex. 2 | 92 |

As shown in Table 2, the compounds of the present invention had longer oxygen absorption induction period, and were superior in heat stability and prevention of degradation due to oxidation, as compared with the compounds of Comparative Examples.

EXPERIMENTAL EXAMPLE 3

Pellets are prepared from polypropylene powder (homopolymer without additives) and the compound of the present invention using an extruder (20 mmφ) at a die temperature of 260° C. These pellets are press-formed at 180° C. to give a pressed plate, from which a test piece (12.7 cm×12.7 cm×0.4 mm) is produced. Using this piece, flame resistance can be determined according to JIS-K-6911-A.

22

An improved flame resistance can be achieved by adding the compound of the present invention to organic materials.

The compound of the present invention is less volatile at high temperatures. The use of the compound of the present invention as a stabilizer for organic materials leads to superior heat stability of the organic material, as well as prevention of degradation thereof due to oxidation. In particular, suppression of migration thereof from the organic materials is conducive to the long lasting effects, and an extremely effective organic material can be obtained.

What is claimed is:

1. A compound of the formula $$X^1 \underset{X^2}{\overset{(O)_p}{\underset{\|}{P}}} - \left[ \phantom{x} \right] - \underset{X^3}{\overset{(O)_q}{\underset{\|}{P}}} - X^4 \quad (I)$$

wherein $X^1$, $X^2$ and $X^4$ are each independently a group of the formula $$-O - \underset{R}{\overset{(H_3C)_3C}{\underset{}{\bigodot}}} - C(CH_3)_3$$

wherein R is a hydrogen atom or a methyl group, $X^3$ is independently, with regard to each repeat unit, a group of the formula $$-O - \underset{R}{\overset{(H_3C)_3C}{\underset{}{\bigodot}}} - C(CH_3)_3$$

wherein R is a hydrogen atom or a methyl group, p is 0 or 1, q is independently 0 or 1 with regard to each repeat unit, and m is an integer of 2–10.

2. A compound of the formula (II)

$$X^1 \underset{X^2}{\overset{(O)_p}{\underset{\|}{P}}} - \left[ \phantom{x} \right] - \underset{X^3}{\overset{(O)_q}{\underset{\|}{P}}} - \left[ \phantom{x} \right] - \underset{X^5}{\overset{(O)_r}{\underset{\|}{P}}} - X^4 \quad (II)$$

wherein $X^1$, $X^2$, $X^3$, $X^4$ and $X^5$ are each independently a group of the formula $$-O - \underset{R}{\overset{(H_3C)_3C}{\underset{}{\bigodot}}} - C(CH_3)_3$$

wherein R is a hydrogen atom or a methyl group, and p, q and r are each independently 0 or 1.

3. A compound of the formula (III)
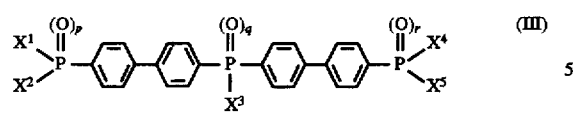 (III)
wherein $X^1$, $X^2$, $X^3$, $X^4$ and $X^5$ are each independently a group of the formula
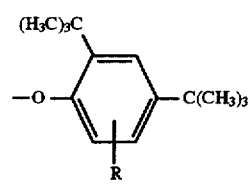
wherein R is a hydrogen atom or a methyl group, and p, q and r are each independently 0 or 1.
* * * * *